(12) United States Patent
Ishikawa

(10) Patent No.: US 9,597,481 B2
(45) Date of Patent: Mar. 21, 2017

(54) CATHETER WITH AN INNER LAYER, REINFORCING LAYER, AND OUTER LAYER

(71) Applicant: ASAHI INTECC CO., LTD., Nagoya-shi, Aichi (JP)

(72) Inventor: Masatomo Ishikawa, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 14/711,114

(22) Filed: May 13, 2015

(65) Prior Publication Data

US 2015/0335857 A1 Nov. 26, 2015

(30) Foreign Application Priority Data

May 21, 2014 (JP) ................................. 2014-104918

(51) Int. Cl.
*A61M 25/01* (2006.01)
*A61M 25/00* (2006.01)

(52) U.S. Cl.
CPC ...... *A61M 25/0045* (2013.01); *A61M 25/005* (2013.01); *A61M 2025/006* (2013.01); *A61M 2025/0062* (2013.01); *A61M 2210/12* (2013.01)

(58) Field of Classification Search
CPC ............ A61M 25/0045; A61M 25/005; A61M 2025/006; A61M 2005/0062; A61M 2210/12

(Continued)

(56) References Cited

U.S. PATENT DOCUMENTS 6,673,025 B1 * 1/2004 Richardson ........... A61M 25/09
600/585
7,909,779 B2 * 3/2011 Shimogami ....... A61M 25/0012
600/585

(Continued)

FOREIGN PATENT DOCUMENTS

EP 1 120 127 A1 8/2001
EP 2174685 A1 4/2010

(Continued)

OTHER PUBLICATIONS

Nov. 2, 2015 Extended European Search Report issued in European Patent Application No. 15163480.5.

(Continued)

*Primary Examiner* — Nathan R Price
*Assistant Examiner* — John Doubrava
(74) *Attorney, Agent, or Firm* — Oliff PLC

(57) ABSTRACT

A catheter includes an inner layer, a coil body covering the inner layer, and an outer layer covering the coil body. The coil body includes a plurality of element wires (thin wires and thick wires). The thick wires of the coil body are ground so that the cross-sectional shape of the thick wires is semicircular, and an inner diameter and an outer diameter of the coil body are substantially constant in a part in which the thick wires are ground. It is thus possible to prevent occurrence of unevenness on an outer peripheral surface or an inner peripheral surface of the catheter. Furthermore, when the catheter is bent, the thin wires move along the circular arc portion of the thick wires, which allows the catheter to bend a relatively large amount.

2 Claims, 6 Drawing Sheets

(58) Field of Classification Search
USPC .......................................................... 604/526
See application file for complete search history.

(56) References Cited

U.S. PATENT DOCUMENTS

| | | | | |
|---|---|---|---|---|
| 8,113,916 | B2* | 2/2012 | Miller | A61M 25/09 |
| | | | | 451/48 |
| 8,540,695 | B2* | 9/2013 | Shimogami | A61M 25/005 |
| | | | | 604/525 |
| 9,339,629 | B2* | 5/2016 | Watanabe | A61M 25/005 |
| 2001/0044633 | A1* | 11/2001 | Klint | A61B 17/12022 |
| | | | | 606/200 |
| 2004/0082879 | A1* | 4/2004 | Klint | A61B 17/12022 |
| | | | | 600/585 |
| 2005/0115624 | A1* | 6/2005 | Walak | A61M 25/0009 |
| | | | | 138/139 |
| 2007/0208368 | A1 | 9/2007 | Katoh et al. | |
| 2009/0281610 | A1 | 11/2009 | Parker | |
| 2011/0144538 | A1* | 6/2011 | Shimogami | A61M 25/09 |
| | | | | 600/585 |
| 2011/0245775 | A1 | 10/2011 | Tekulve | |

FOREIGN PATENT DOCUMENTS

| | | | |
|---|---|---|---|
| JP | 2007236472 A | 9/2007 | |
| JP | 2011-110144 A | 6/2011 | |
| JP | 2012-061070 A | 3/2012 | |

OTHER PUBLICATIONS

Nov. 14, 2016 Office Action issued in Japanese Patent Application No. 2014-104918.

\* cited by examiner

CATHETER WITH AN INNER LAYER, REINFORCING LAYER, AND OUTER LAYER

CROSS REFERENCE TO RELATED APPLICATION

This application claims priority to Japanese Patent Application No. 2014-104918 filed in the Japan Patent Office on May 21, 2014, the entire contents of which are incorporated herein by reference.

BACKGROUND

The disclosed embodiments relate to a catheter that may be inserted in, for example, a blood vessel.

Catheters that are inserted in a lumen of a blood vessel are well known in the art. With such catheters, a physician injects liquid chemicals or a contrast agent into a blood vessel. Additionally or alternatively, the physician sends various devices (for example, a stent or an embolic coil) to a lesion of a blood vessel.

Traditionally, catheters include a resin tube and various reinforcing bodies reinforcing the tube. For example, European Patent Application Publication No. EP 1 120 127 A1 describes that a coil body formed by winding a plurality of element wires into a helical coil structure is used as a reinforcing body of a catheter. Moreover, U.S. Publication No. 2007/0208368 discloses a technique of improving rotation transmission performance and press-in performance (pushability) of a catheter by using, as some of a plurality of element wires constituting the coil body, thicker element wires (thick wires) than other element wires (thin wires).

SUMMARY

However, in the traditional catheters, an outer peripheral surface or an inner peripheral surface of the coil body becomes uneven due to the thin wires and the thick wires that form the coil body. This causes a problem of increasing sliding resistance between the outer peripheral surface of the catheter and an inner wall of, for example, a blood vessel or a lesion. Additionally, the uneven coil body may cause the problem of increasing sliding resistance between the inner peripheral surface of the catheter and a combined device, such as a guide wire. In addition, the uneven coil body makes it difficult to sufficiently adhere a coating to the outer peripheral surface and/or the inner peripheral surface of the coil body.

The disclosed embodiments prevent and/or reduce the occurrence of unevenness on an outer peripheral surface or an inner peripheral surface of a catheter that includes a coil body formed of thick wires and thin wires.

The disclosed embodiments include a tube body having an inner layer, a reinforcing layer covering the inner layer, and an outer layer covering the reinforcing layer. The reinforcing layer is a coil body formed by winding a plurality of element wires into a helical coil structure, the element wires including thin wires and thick wires. At least a part of the thick wires are ground so that a cross-sectional shape of the thick wires is substantially semicircular, and an inner diameter and an outer diameter of the coil body are substantially constant in the part in which the thick wires are ground.

In some disclosed embodiments, the catheter includes a part in which the thick wires are ground so that the cross-sectional shape thereof is a substantially semicircular shape, and an inner diameter and an outer diameter of the coil body in this part are constant. Thus, no unevenness occurs on the outer peripheral surface (or the inner peripheral surface) of the coil body. It may therefore be possible to suppress sliding resistance on the surface of the catheter and secure adhesion of a coating.

When the catheter is bent, the thin wires move along the circular arc portion of the thick wires, which allows the catheter to bend a large amount. As a result, it is possible to exert favorable following properties even for a largely bent blood vessel.

Moreover, the straight portion of the substantially semicircular shape of the thick wires may be disposed on the outer peripheral side of the coil body.

In some disclosed embodiments, the straight portion of the section (substantially semicircular shape) of the thick wires is disposed on the outer peripheral side of the coil body. Thus, it is possible to easily produce the catheter of the disclosed embodiments only by forming the coil body by wiring thick wires and thin wires and then grinding the thick wires from the outer peripheral side of the coil body.

Moreover, a part in which the thick wires are ground may be provided at the distal end portion of the coil body, and a part in which the thick wires are not ground may be provided at the proximal end portion of the coil body. In the part in which the thick wires are not ground, the thick wires may project outward on the outer peripheral side of the coil body.

In such a catheter of the disclosed embodiments, a part in which the thick wires are ground (a part with a smooth surface) is provided at the distal end portion of the coil body, and a part in which the thick wires are not ground and project on the outer peripheral side (a part with an uneven surface) is provided at the proximal end portion of the coil body. Therefore, it may be possible to easily suppress sliding resistance at the distal and proximal end portions of the catheter and thus fix the catheter at a desired position.

DETAILED DESCRIPTION OF EMBODIMENTS

Figure 1:
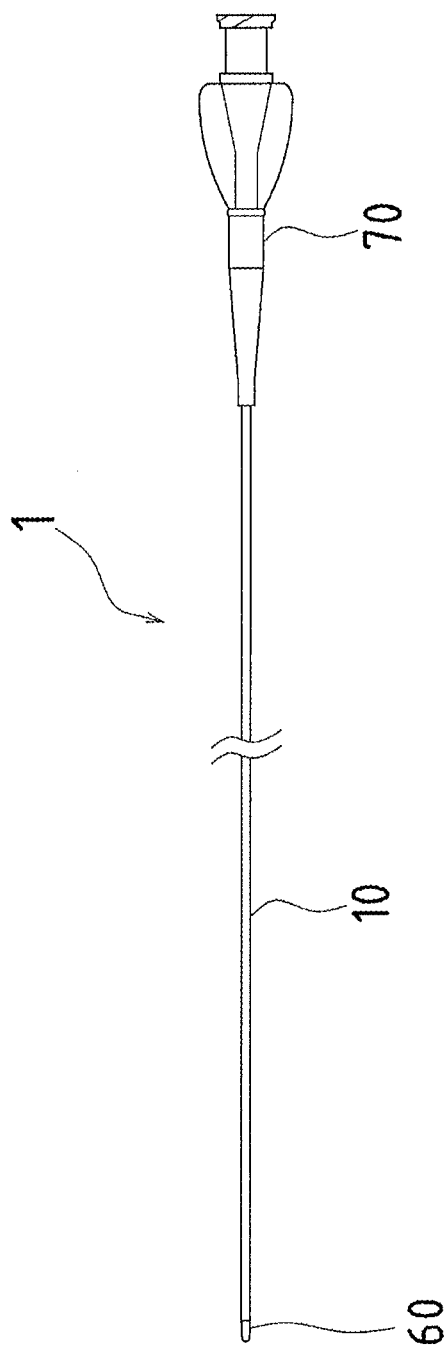
FIG. 1 schematically illustrates a catheter according to embodiments.

As illustrated in FIG. 1, catheter 1 may include a catheter shaft 10, a tip 60 provided at the distal end of the catheter shaft 10, and a connector 70 provided at the proximal end of the catheter shaft 10.

Note that the "catheter shaft" corresponds to a "tube body."

Figure 2:
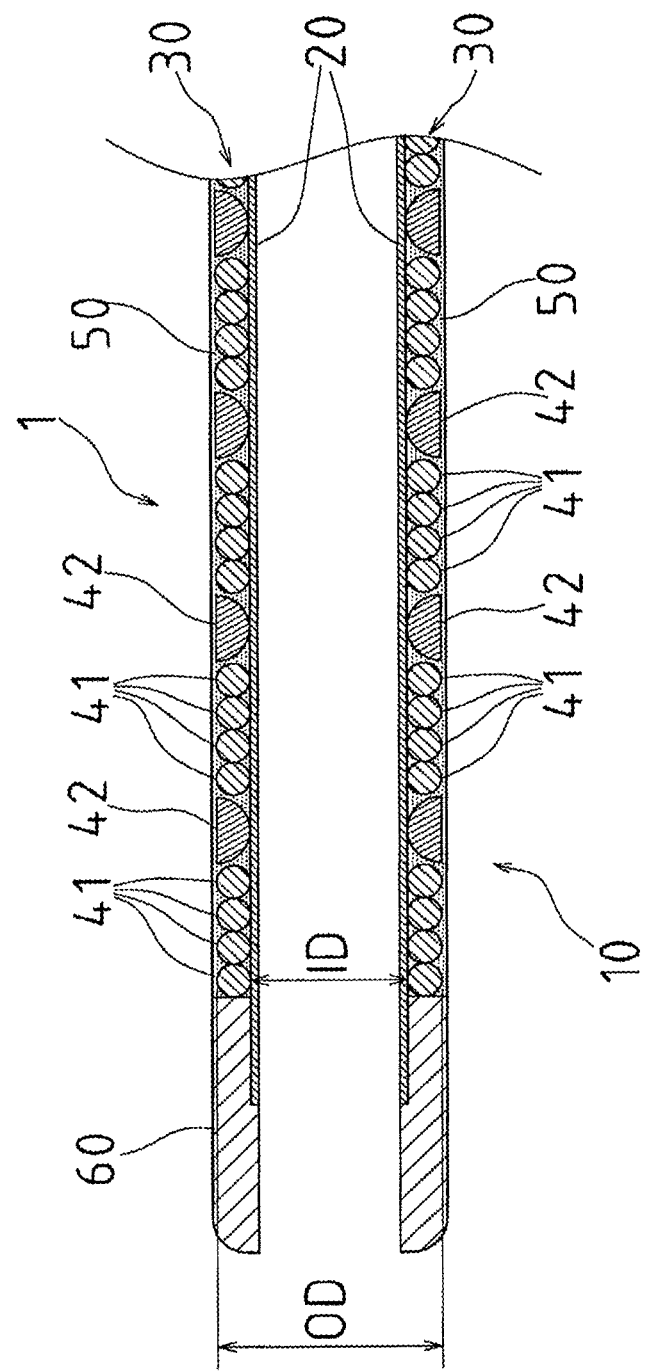
FIG. 2 is a cross-sectional view of the catheter of FIG. 1.

As illustrated in FIG. 2, the catheter shaft 10 is a tubular structural body that may include an inner layer 20, a coil body 30 as a reinforcing layer covering the inner layer 20, and an outer layer 50 covering the coil body 30.

The inner layer 20 may be formed of resin. The resin material forming the inner layer 20 is not especially limited. However, polytetrafluoroethylene (PTFE) is a preferred material considering slidability with an inserted instrument (for example, a guide wire or a catheter).

The outer layer 50 may also be formed of resin. The resin material forming the outer layer 50 is not especially limited, and may include, for example, polyamide, polyamide elastomer, polyester, and/or polyurethane.

The coil body 30 may be formed by winding two kinds of element wires having different element wire diameters (i.e., thin wires 41 and thick wires 42) into a helical coil structure.

The material of element wires 41, 42 constituting the coil body 30 is not especially limited, and may include, for example, stainless steel (SUS304, SUS316, etc.), gold, white gold, tungsten, platinum, nickel, and/or an alloy of such elements.

The tip 60 may be disposed at the distal end of the catheter shaft 10. The resin forming the tip 60 is not especially limited. However, polyurethane, polyurethane elastomer, etc. are preferred materials. Moreover, the tip 60 may contain radiopaque powder (for example, tungsten powder) to enable a physician to accurately determine a position of the catheter during, for example, coronary angiography.

The thick wires 42 of the coil body 30 may be ground so that they have a cross-sectional shape that is substantially semicircular, as shown, for example, in FIG. 2. Thus, the surface(s) of the thick wires 42 may be ground by an external device so that the surface(s) is substantially smooth. The grounding of the thick wires 42 may be formed by, for example, sanding, a grinder, chemical means, or other mechanical means. The semicircular shape of the thick wires 42 allows the inner diameter ID and the outer diameter OD of the coil body 30 to be substantially constant. For example, as shown in FIG. 2, the inner diameter ID and the outer diameter OD are both substantially even. Therefore, the outer peripheral surface (or the inner peripheral surface) of the coil body 30 may be even so that substantially no unevenness occurs. Thus, it may be possible to prevent and/or reduce the increase of sliding resistance between the outer peripheral surface of the catheter 1 and an inner wall of, for example, a blood vessel or a lesion. It may also be possible to prevent and/or reduce an increase of sliding resistance between the inner peripheral surface of the catheter 1 and a combined device, such as a guide wire.

Because the surface of the coil body 30 has substantially no unevenness, it may be possible to securely adhere a coating, for example outer layer 50, on the coil body 30.

Figure 3:
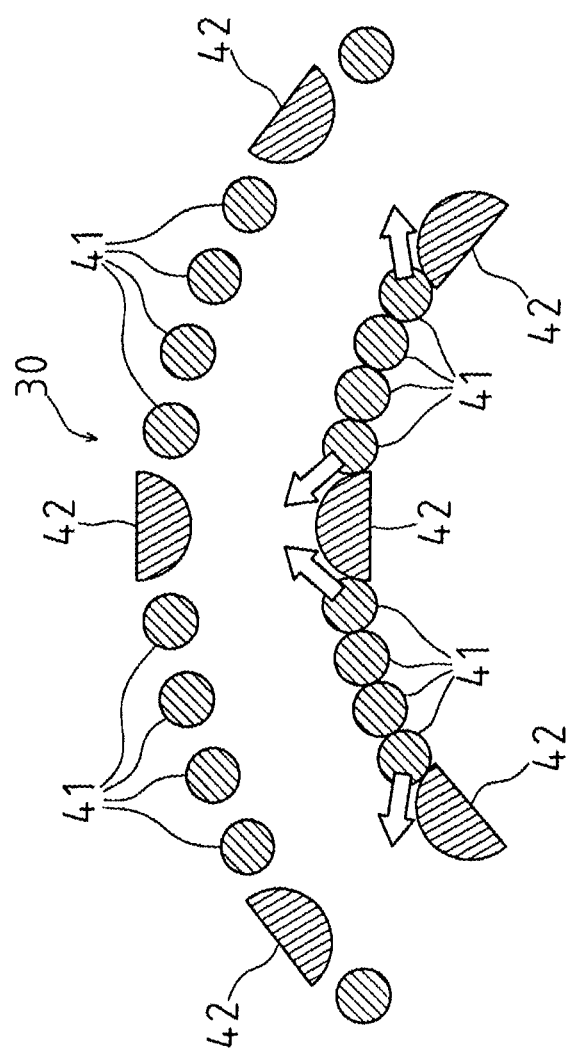
FIG. 3 is another cross-sectional view of the catheter of FIG. 1 showing what may occur during bending.

FIG. 3 depicts a situation when the coil body 30 of the catheter 1 is bent. As shown in FIG. 3, when the coil body 30 is bent, the element wires 41, 42 on the bent side (the lower side in FIG. 3) may experience increased force in a direction that compresses the coil body 30. As shown by the arrows in FIG. 3, the thin wires 41 adjacent to the thick wires 42 may slightly move to the lumen side of the coil body 30 as the thin wires 41 are pushed out along the circular arc portion of the thick wires 42.

In this manner, when the coil body 30 is bent, the thin wires 41 may move along the circular arc portion of the thick wires 42, which prevents stretching of the coil body 30 and allows the coil body 30 (and thus the catheter 1) to bend a large amount. More specifically, such may allow the coil body 30 (and thus the catheter 1) to assume relatively large bent shapes. As a result, the catheter 1 may be used in blood vessel with such relatively large bent shapes.

As shown in FIG. 2, the straight (flat) portion of the substantially semicircular shape of the thick wires 42 is disposed on the outer peripheral side of the coil body 30.

Figure 4:
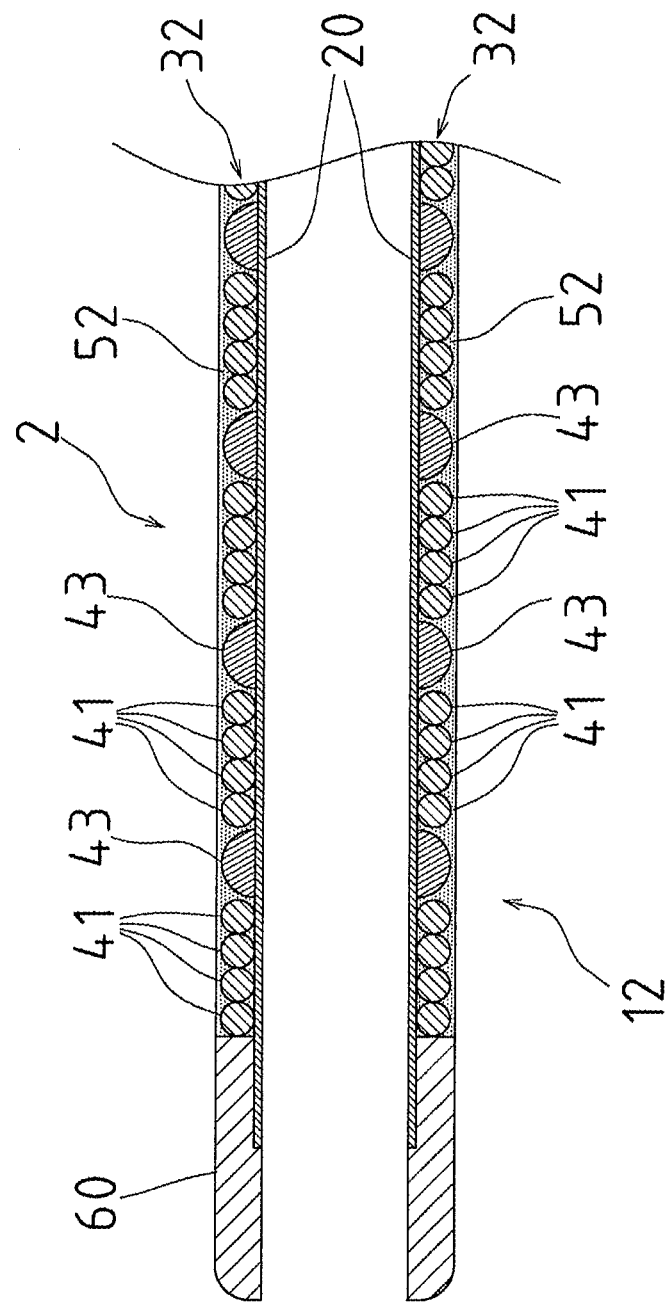
FIG. 4 is a cross-sectional view of a modification of the catheter of FIG. 1.

As shown in FIG. 4, catheter 2 may include catheter shaft 12 such that the straight (flat) portion of the semicircular shape of the thick wires 43 is disposed on the inner peripheral side of coil body 32

The catheter 1, as shown in FIG. 1, may be easily produced because the straight portion of the substantially semicircular shape of the thick wires 42 is disposed on the outer peripheral side of the coil body 30 (see FIG. 2), and thus it may be possible to easily produce the coil body 30 by wiring the thick wires 42 and the thin wires 41 into a helical coil structure and then grinding the thick wires 42 from the outer peripheral side of the coil body.

Figure 5:
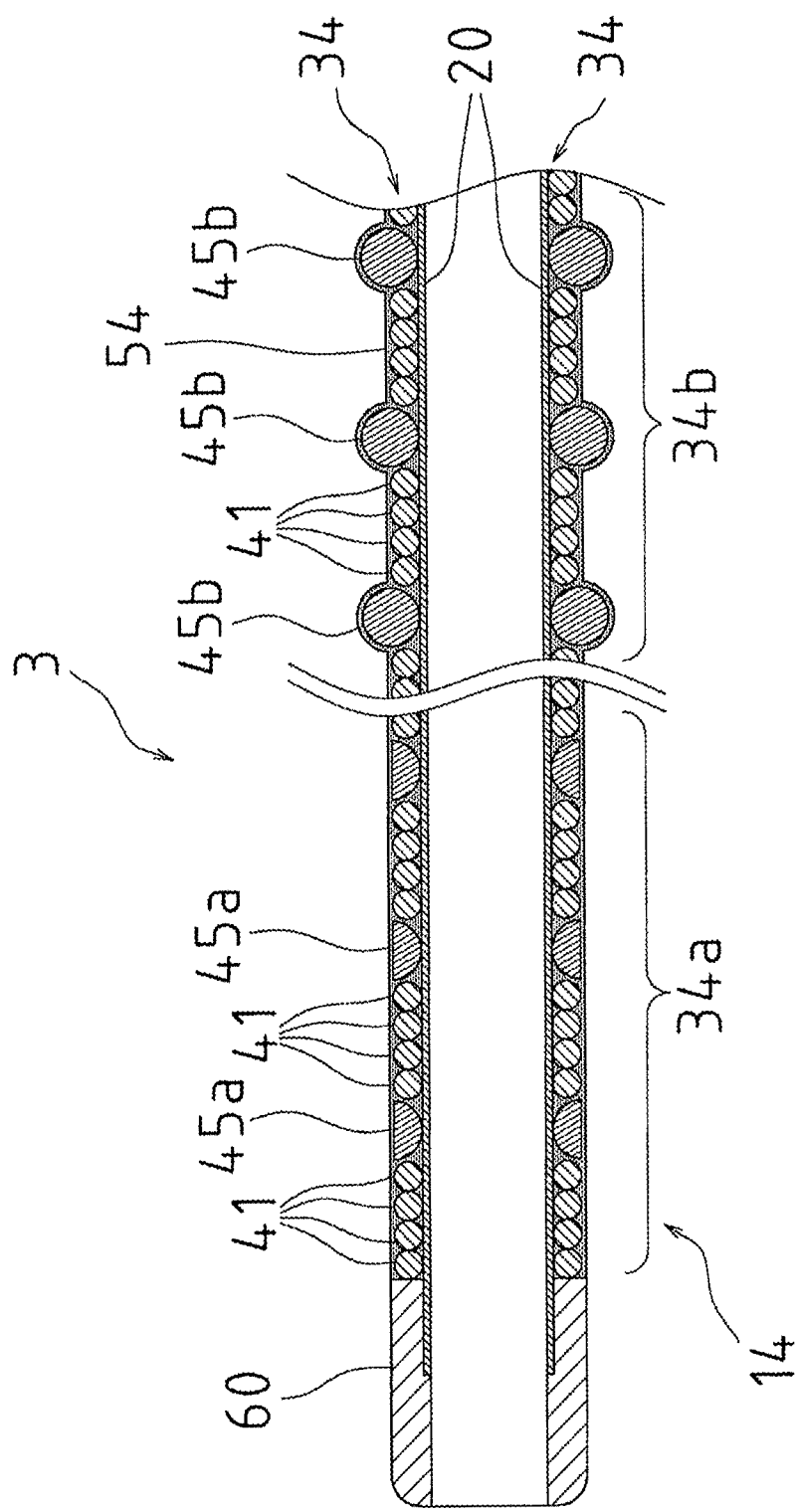
FIG. 5 is a cross-sectional view of a modification of the catheter of FIG. 1.

As shown in FIG. 5, catheter 3 may include catheter shaft 14 that includes coil body 34 with thick wires 45a. The thick wires 45a may be ground at a distal end portion of the coil body 34 so that the thick wires 45a have a cross-sectional shape that is substantially semicircular. Additionally, coil body 34 may include thick wires 45b that are not ground at a proximal end portion 34b of the coil body 34. As shown in FIG. 5, because the thick wires 45b are not ground, the thick wires 45b may project outward on the outer peripheral side of the coil body 34, thus forming unevenness on the outer peripheral surface.

The catheter shaft 14, as shown in FIG. 5, may include the inner layer 20, the coil body 34 covering the inner layer 20, and an outer layer 54 covering the coil body 34. Additionally, the coil body 34 may include the thin wires 41 and the thick wires 45a, 45b. The tip 60 may be provided at the distal end of the catheter shaft 14.

When the distal end portion 34a of the coil body 34 is bent, the thin wires 41 may move along the circular arc portion of the thick wires 45a, which allows the catheter 3 to bend a large amount. More specifically, such may allow the coil body 34 (and thus the catheter 3) to assume relatively large bent shapes. In this manner, the catheter 3 may exert, at the distal end portion 34a, favorable sliding properties relative to an inner wall of a blood vessel and favorable following properties for a blood vessel.

The thick wires 45b are not ground at the proximal end portion 34b of the catheter 3, and thus unevenness may form on the outer peripheral surface of the coil body 34, as shown in FIG. 5. This may moderately increase and thus secure sliding resistance at the proximal end portion 34b of the catheter 3, which makes it possible to easily fix the catheter 3 inserted in, for example, a lumen of a blood vessel at a desired position.

Figure 6:
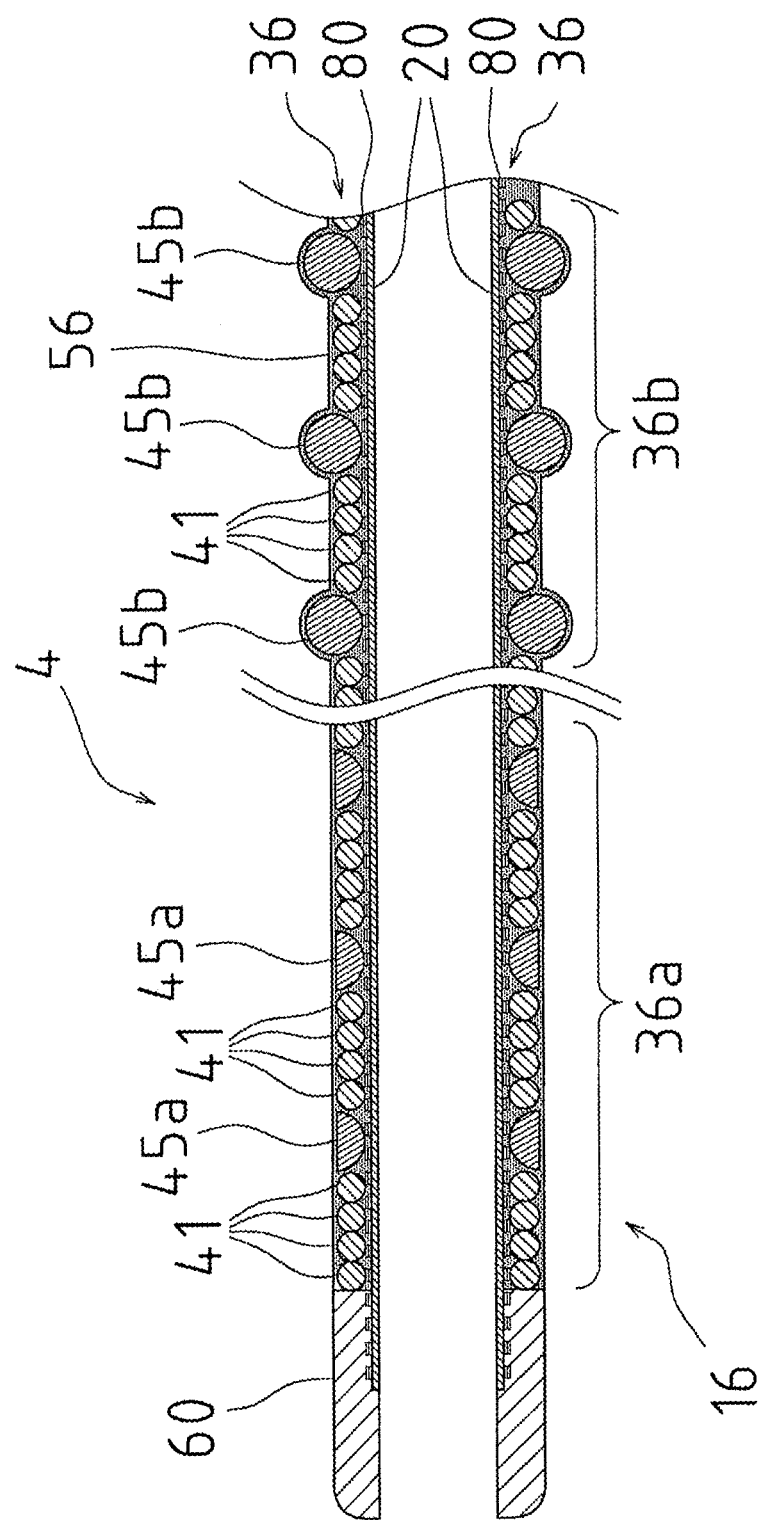
FIG. 6 is a cross-sectional view of a modification of the catheter of FIG. 1.

As shown in FIG. 6, catheter 4 may include catheter shaft 16 that includes inner layer 20 covered by a braid layer 80, which is formed by braiding metal wires. Additionally, the braid layer 80 may be covered by a coil body 36, which is covered by an outer layer 56.

The coil body 36 may include the thin wires 41 and the thick wires 45a, 45b such that the thick wires 45a are ground at a distal end portion 36a of the coil body 36 and the thick wires 45b are not ground at a proximal end portion 36b of the coil body 36. Tip 60 may be provided at the distal end of the catheter shaft 16.

The braid layer 80 may form a reinforcing layer of the catheter 4, in addition to the coil body 36, in order to increase the rigidity of the catheter shaft 16. In particular, at the distal end portion 36a of the coil body 36, the reduced rigidity, caused by grinding of the thick wires 45, may be compensated by the braid layer 80. As a result, it is possible to easily transmit push-in force added by a technician in a distal end direction to the tip 60.

What is claimed is:
1. A catheter, comprising:
a tube body including an inner layer, a reinforcing layer covering the inner layer, and an outer layer covering the reinforcing layer, wherein:

the reinforcing layer is a coil body formed by winding a plurality of element wires into a helical coil structure, the element wires including first wires and second wires, a cross-sectional shape of the first wires is circular, a cross-sectional shape of the second wires is semicircular with a straight side and a rounded side, and a diameter of the first wires is substantially the same as a maximum length between the straight side and the rounded side of the second wires.

2. The catheter according to claim 1, wherein the straight side of the semicircular cross-sectional shape of the second wires is disposed on an outer peripheral side of the coil body.

\* \* \* \* \*